(12) United States Patent
Weiler

(10) Patent No.: US 11,684,409 B2
(45) Date of Patent: Jun. 27, 2023

(54) ELECTROSURGICAL INSTRUMENT WITH JOINT SEAL

(71) Applicant: Erbe Elektromedizin GmbH, Tuebingen (DE)

(72) Inventor: Rolf Weiler, Tuebingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 393 days.

(21) Appl. No.: 16/849,481

(22) Filed: Apr. 15, 2020

(65) Prior Publication Data

US 2020/0330148 A1    Oct. 22, 2020

(30) Foreign Application Priority Data

Apr. 17, 2019   (EP) ..................... 19169865

(51) Int. Cl.
*A61B 18/14*   (2006.01)
*A61B 17/29*   (2006.01)

(52) U.S. Cl.
CPC .. *A61B 18/1442* (2013.01); *A61B 2017/2947* (2013.01); *A61B 2017/2948* (2013.01); *A61B 2018/1455* (2013.01)

(58) Field of Classification Search
CPC ........ A61B 18/1445; A61B 2018/0063; A61B 2018/1455; A61B 18/1442; A61B 2017/2947; A61B 2017/2948
See application file for complete search history.

(56) References Cited

U.S. PATENT DOCUMENTS

| 5,484,436 A | 1/1996 | Eggers et al. |
| 9,333,004 B2 * | 5/2016 | Brückler ........ A61B 17/320016 |

(Continued)

FOREIGN PATENT DOCUMENTS

| EP | 1372512 A1 | 1/2004 |
| EP | 1372512 B1 | 6/2005 |

(Continued)

OTHER PUBLICATIONS

European Intent to Grant dated Dec. 13, 2021, in corresponding European Application No. 19169865.3, with machine English translation (12 pages).

(Continued)

*Primary Examiner* — Anna K Kinsaul
*Assistant Examiner* — Veronica Martin
(74) *Attorney, Agent, or Firm* — Fitch, Even, Tabin & Flannery LLP

(57) ABSTRACT

An electrosurgical instrument (10) with two branches (11, 12) that are pivotably supported at each other by means of a pivot joint (13) is disclosed. The pivot joint (13) has a support pin (34) and a support cavity (37). The support pin (34) is particularly torque-proof connected with one of the branches (11) or (12) and rotatably supported in the support cavity (37) of the respective other branch (12) or (11). Between the branches (11, 12) a seal (45) is provided that sealingly abuts at the two branches (11, 12) and that surrounds the support pin (34) completely in the circumferential direction. Preferably, the support pin (34) is sealingly connected with the respective branch (11, 12) at its axial ends. In doing so, entering of contaminants in the area between the support pin (34) and the support cavity (37) from all sides or access possibilities is inhibited.

13 Claims, 6 Drawing Sheets

(56) References Cited

U.S. PATENT DOCUMENTS

| | | | | |
|---|---|---|---|---|
| 10,893,914 B2* | 1/2021 | Boudreaux | ............ | A61B 17/285 |
| 2013/0190753 A1* | 7/2013 | Garrison | ................. | A61B 18/12 |
| | | | | 606/41 |
| 2014/0214019 A1* | 7/2014 | Baxter, III | ......... | A61B 17/3201 |
| | | | | 606/41 |
| 2016/0157921 A1* | 6/2016 | Ding | ................... | A61B 18/1442 |
| | | | | 606/208 |
| 2018/0132884 A1 | 5/2018 | Denzinger et al. | | |

FOREIGN PATENT DOCUMENTS

| | | |
|---|---|---|
| EP | 2366353 A1 | 9/2011 |
| WO | 02/080798 A1 | 10/2002 |
| WO | 2019/028647 A1 | 2/2019 |

OTHER PUBLICATIONS

European Extended Search Report dated Oct. 29, 2019, in corresponding European Application No. 19169865.3, with machine English translation (11 pages).

* cited by examiner

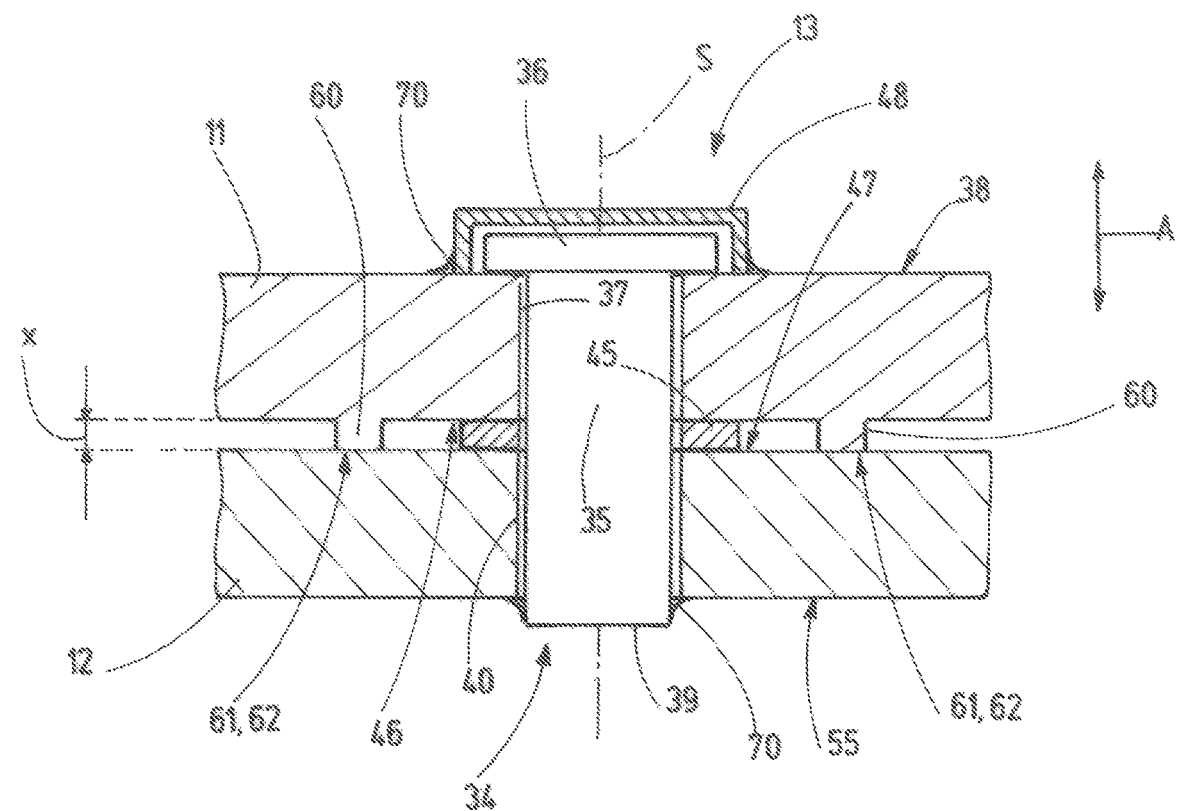

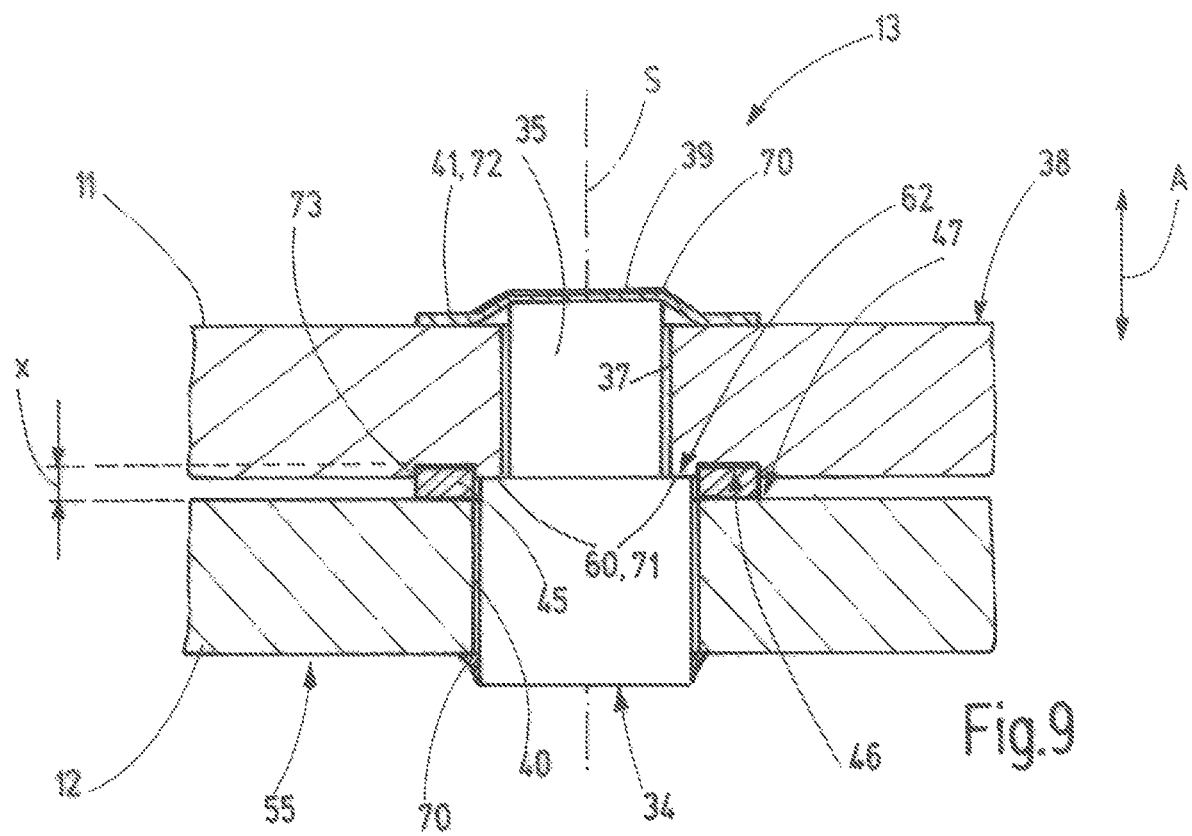
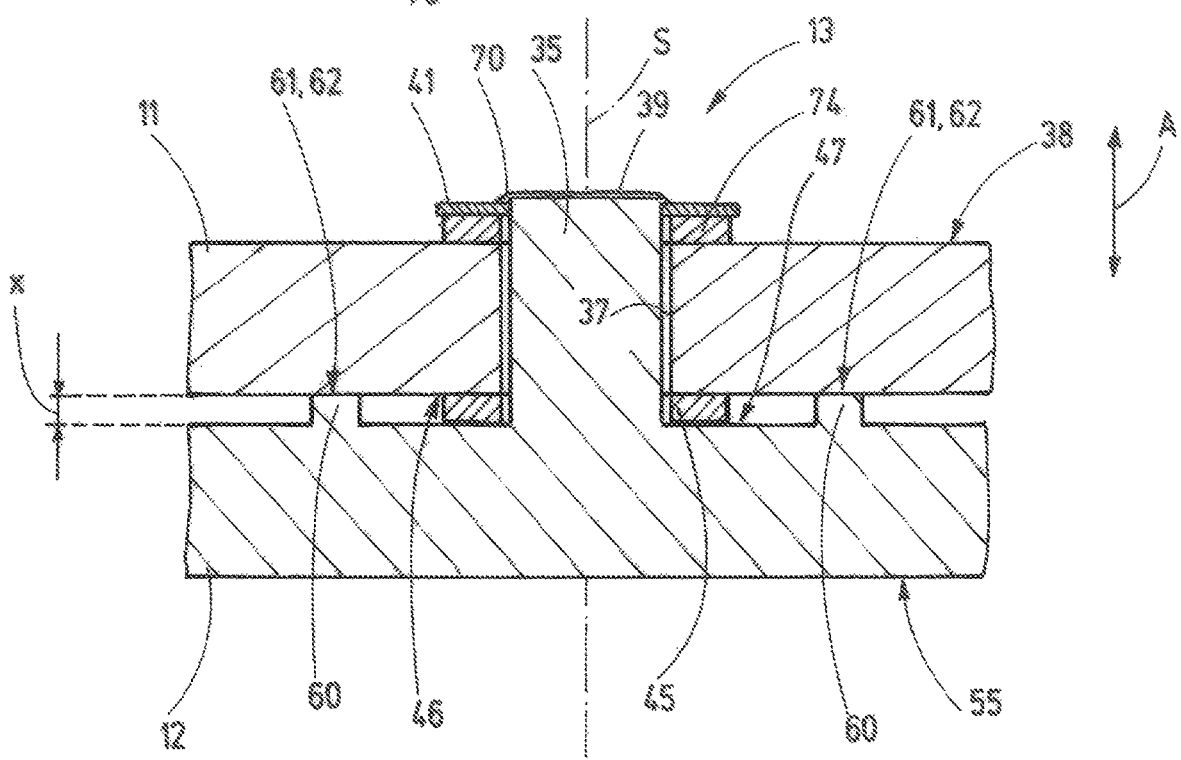

ELECTROSURGICAL INSTRUMENT WITH JOINT SEAL

RELATED APPLICATION(S)

This application claims the benefit of European Patent Application No. 19169865.3, filed Apr. 17, 2019, the contents of which are incorporated herein by reference as if fully rewritten herein.

TECHNICAL FIELD

The invention refers to an electrosurgical instrument that can be used for thermal fusion and/or for sealing or coagulation for example. The electrosurgical instrument has two branches, each having a jaw. Each jaw comprises a tissue contact surface. Via the tissue contact surfaces a current can be conducted through tissue that is clamped between the tissue contact surfaces, e.g. in order to seal the tissue.

BACKGROUND

Such electrosurgical instruments are known. EP 1 372 512 B1 discloses an instrument with two branches, each comprising a jaw and articulated at each other.

Electrosurgical instruments can be provided as single-use instruments or multiple-use instruments. In some countries also single-use instruments are reprocessed for further use by specific providers. Multiple-use instruments are provided for a plurality of applications anyhow and must be sanitized and reprocessed after each use.

It can be considered an object of the present invention to provide an electrosurgical instrument with two branches pivotably supported at each other that guarantees a simplified cleaning and/or sterilization.

SUMMARY

The electrosurgical instrument has a first branch and a second branch. The two branches are pivotably supported at each other about at least one pivot axis by at least one pivot joint. The at least one pivot joint has a support pin and a support cavity. The support pin extends into the support cavity and particularly defines the pivot axis. According to the invention, a seal is present between the two branches at the pivot joint. The seal surrounds the pivot pin completely in circumferential direction about the pivot axis. The seal has a sealing effect in an axial direction. The axial direction is orientated parallel to the pivot axis. The seal abuts sealingly in axial direction at the first branch and the second branch. Abutment surfaces of the first and the second branch against which the seal abuts can be orientated parallel to each other.

By means of the seal, the pivot joint is sealed between the branches. Contaminants cannot enter between the branches into a gap surrounding the pivot pin or the entering of contaminants is at least mitigated by the seal. However, the seal guarantees that a gap or interstice can remain between the branches such that the area between the branches is sufficiently accessible for cleaning.

Preferably the seal is temperature-resistant for temperatures of at least 140° C. The seal is particularly permeable for steam and ethylene oxide (ETO). In doing so, sterilization is not hindered by the seal.

In one embodiment the seal consists of silicon.

The seal can have a hardness of 60 Shore.

For example, the seal can have a rectangular cross-section. The seal can be referred to as seal disc.

Preferably the seal is elastically deformed in axial direction such that the seal is compressed between the branches. In doing so, a pressure force between the seal and the branches is created. This pressure force creates a good sealing effect.

The first branch can comprise a first abutment surface for abutment of the seal and the second branch can comprise a second abutment surface for abutment of the seal. The abutment surfaces surround the support pin at the first branch or the second branch respectively.

Preferably at least one distance element is present. The at least one distance element extends in axial direction parallel to the pivot axis and defines an axial distance between the first abutment surface of the first branch and the second abutment surface of the second branch. For example, the axial distance can have a length of 0.1 mm to 0.4 mm. In one embodiment the axial distance has a length of 0.2 mm. The first and second abutment surface are preferably orientated parallel to each other.

The area of the pivot joint can be shielded or covered by the branches independent from the opening angle of the branches. Therefore, this area cannot be directly cleaned or wiped, e.g. by a brush, even if the branches are arbitrarily widely opened. It is thus inaccessible for mechanical cleaning. Due to the at least one distance element, a defined gap or interstice remains between the two branches in the area of the pivot joint. The accessibility as far as the seal is thus improved. In addition, a defined axial compression or elastic deformation of the seal between the two branches can be predefined or achieved by the at least one distance element. The at least one distance element can in addition improve the joint stability and avoid a twisting and/or a warp and/or tilting of the branches.

In a preferred embodiment the at least one distance element is rigidly connected with one of the branches. The at least one distance element can be an integral part of one of the two branches or of a portion of one of the two branches. For example, this one branch can comprise a plastic part of a plastic coating that comprises or forms the at least one distance element. As an alternative, the at least one distance element can be connected with one of the branches by means of a connection process, e.g. welding, gluing or the like.

The at least one distance element can have an end surface at its free end that can be, for example, orientated rectangular to the pivot axis. The end surface can extend parallel to a plane or can be configured at least in sections convexly spherical or curved. The end surface can form a friction bearing surface. By means of the end surface or the friction bearing surface, the at least one distance element can be in contact at the first branch or the second branch. The end surface or friction bearing surface is sufficiently small such that a small friction is created during a relative movement of the branches. Thus, a friction bearing contact between the two branches is established by the at least one distance element, in order to guarantee the pivotability about the pivot axis. It is preferred, if at least three distance elements and in one embodiment exactly three distance elements are present. The distance elements can be arranged with distance to each other in circumferential direction about the pivot axis. Preferably the distance elements are substantially uniformly distributed about the pivot axis in circumferential direction.

In the non-deformed initial condition the seal has an axial thickness that can be larger than the axial distance between the first abutment surface of the first branch and the second abutment surface of the second branch for creation of the elastic deformation. In one embodiment the axial initial thickness in the non-deformed initial condition is 0.1 mm to 0.2 mm larger than the axial distance. In another embodiment the axial initial thickness in the non-deformed initial condition is about at least 25% or about at least 50% larger than the axial distance. The axial initial thickness of the undeformed seal can be up to 200% larger than the axial distance.

It is also advantageous, if the seal is arranged in at least one depression. The at least one depression can be present in the first branch and/or the second branch. The position of the seal orthogonal or radial to the pivot axis can be predefined by the depression. The first abutment surface and/or the second abutment surface is/are formed by the bottom of the at least one depression. By the at least one depression the axial distance between the abutment surfaces can be increased without the need to increase the axial distance between the two branches and thus the axial dimension of the instrument. In doing so, larger thicknesses for the seal are possible, which leads to a larger compression path or compression travel for the elastic deformation of the seal in axial direction. In doing so, the sealing effect can be improved. In this way manufacturing tolerances can be superiorly compensated. In addition the instrument is less sensitive against use-related changes and external influences, such as shrinkage and/or abrasion of materials in the area of the joint.

In the first branch and/or second branch a knife guide cavity can be provided. The knife guide cavity is configured to support a knife arranged therein in a movement direction movably in a guided manner. The movement direction is orientated orthogonal to the axial direction that is parallel to the pivot axis. In this configuration the pivot pin can be arranged offset to the knife guide cavity.

It is advantageous, if a biasing element is present that urges or presses the first branch and the second branch in axial direction parallel to the pivot axis toward each other. In doing so, tolerances or wear can be compensated and a reliable and defined abutment or sealing effect can be achieved. This means that a biasing effect or biasing force acts on the seal or the area of the joint is fixed. The biasing element is able to readjust, e.g. if the material wears or shrinks in the course of time etc.

In addition to the seal between the two branches, preferably also the support gaps between the support pin and the first branch and/or the second branch are sealed. For example, the pivot pin can be an integral part of one of the branches or can be rigidly and tightly connected with this branch, e.g. can be welded or glued to the branch. Thus, the support pin can be arranged in a torque-proof manner at the branch. The entering of contaminants in a gap around the pivot pin can be avoided, due to the rigid and tight connection at one axial end of the support pin.

An additional further seal element can seal the gap between the support cavity and the support pin rotatably arranged therein with regard to the branch relative to which the support pin is rotatably arranged in the support cavity. This further seal element can be configured analog to the seal. The further seal element can comprise a sealing cover, a fixing element, particularly a fixing disc or the like.

In an alternative embodiment the at least one distance element can be provided at the support pin or can be formed by a portion of the support pin.

In one embodiment of the electrosurgical instrument one branch can form a fork part into which the other branch extends, wherein the support pin passes through both branches in the area of the fork part and pivotably supports the two branches at each other. In this embodiment preferably two seals for the two inner abutment surfaces of the branches are provided. The branch extending into the fork part is arranged between the seals and thus sealed with regard to the fork part of the other branch in the area of the pivot axis on both sides.

BRIEF DESCRIPTION OF THE DRAWINGS

Advantageous embodiments of the invention can be derived from the dependent claims, the specification and the drawings. In the following preferred embodiments of the invention are explained in detail with reference to the attached drawings. The drawings show:

DETAILED DESCRIPTION

Figure 1:
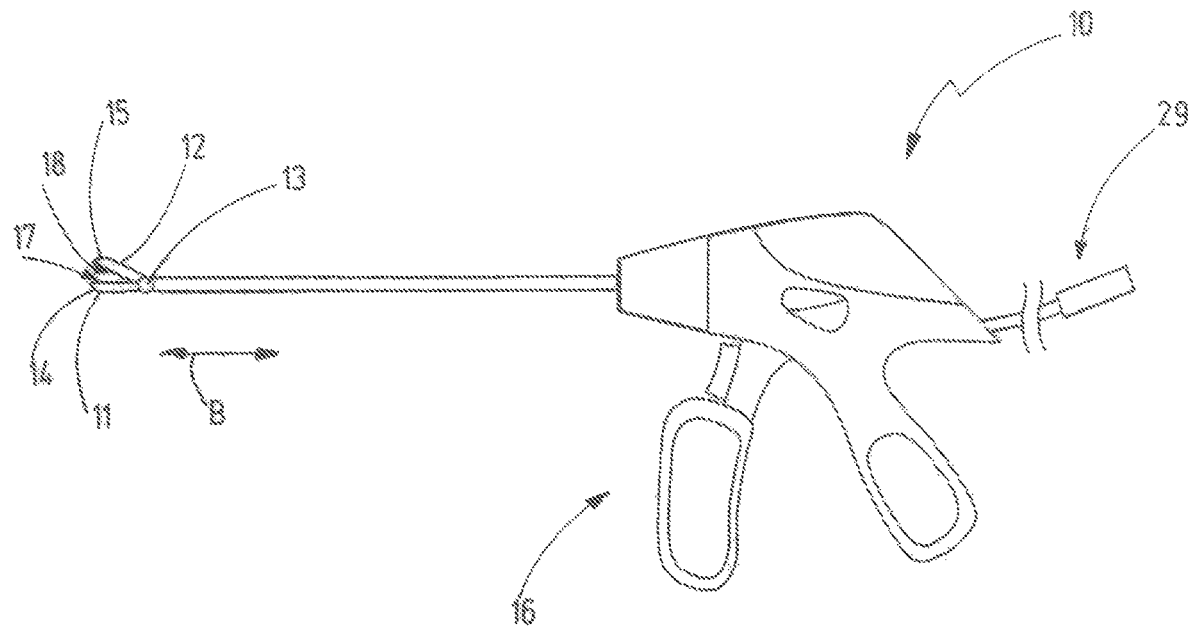
FIG. 1 a schematic side view of an embodiment of an electrosurgical instrument with two branches pivotably supported at each other, FIG. 2 a schematic side view of a further embodiment of an electrosurgical instrument with two branches pivotably supported at each other, FIG. 3 a schematic explosion illustration of the electrosurgical instrument of FIG. 2, FIG. 4 a perspective sectional illustration through an embodiment of a pivot joint for pivotable support of the branches of FIGS. 1-3, FIG. 5 a schematic perspective sectional illustration of another embodiment of a pivot joint for pivotable support of the branches of FIGS. 1-3, FIG. 6 a schematic view of a branch in the area of the pivot joint with view on the surface facing the respective other branch and comprising a knife guide channel and distance elements, FIG. 7-11 one schematic sectional illustration along the pivot axis of different embodiments of pivot joints respectively for pivotable support of the branches of FIGS. 1-3, FIG. 12 a basic diagram for illustration of the axial compression of a seal arranged between the branches.
Figure 2:
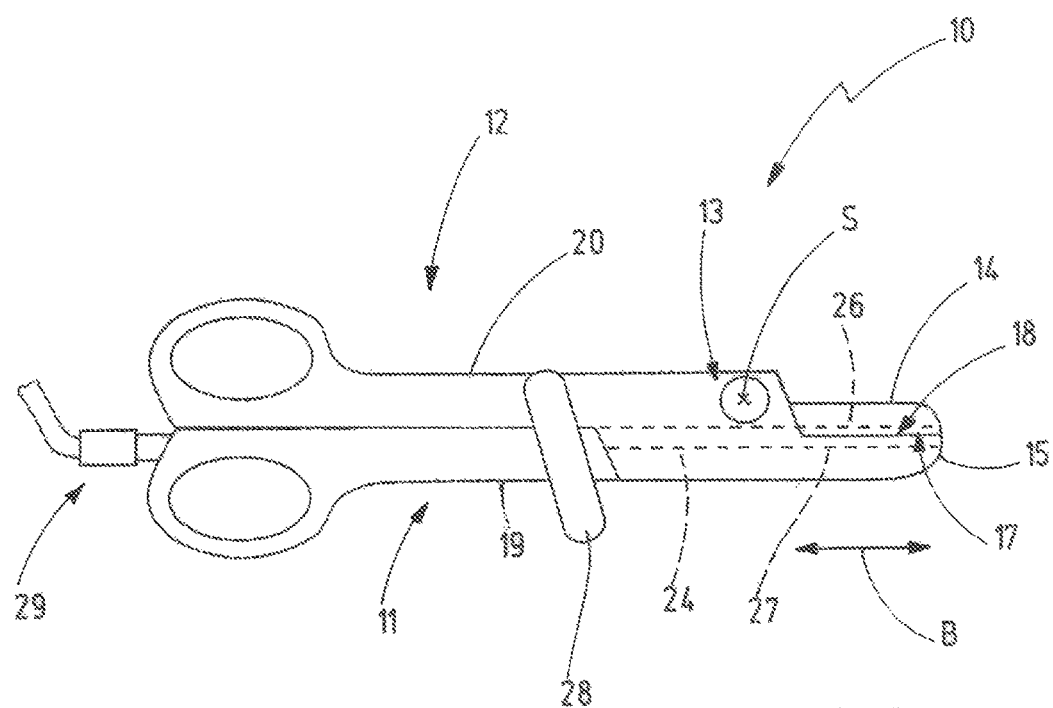

In FIGS. 1 and 2 different embodiments of an electrosurgical instrument 10 are highly schematically illustrated, i.e. for example configured as bipolar instrument. The electrosurgical instrument 10 has a first branch 11 and a second branch 12 that are pivotably supported about a pivot axis S at each other by means of a pivot joint 13. The direction parallel to the pivot axis S is denoted as axial direction A.

In the embodiment illustrated in FIG. 1 mainly the jaws 14, 15 are illustrated that extend originating from the pivot axis S or the pivot joint 13 in a distal section. The first jaw 14 and/or the second jaw 15 can be pivotably supported. For opening or closing the jaws 14, 15 the instrument 10 of FIG. 1 comprises an operation unit 16. By means of the operation unit 16 also further actions can be carried out, e.g. applying a voltage between the first tissue contact surface 17 at the first jaw 14 and a second tissue contact surface 18 at the second jaw 15. In doing so, a current flow through a tissue can be caused that is clamped or held between the two tissue contact surfaces 17, 18.

Figure 3:
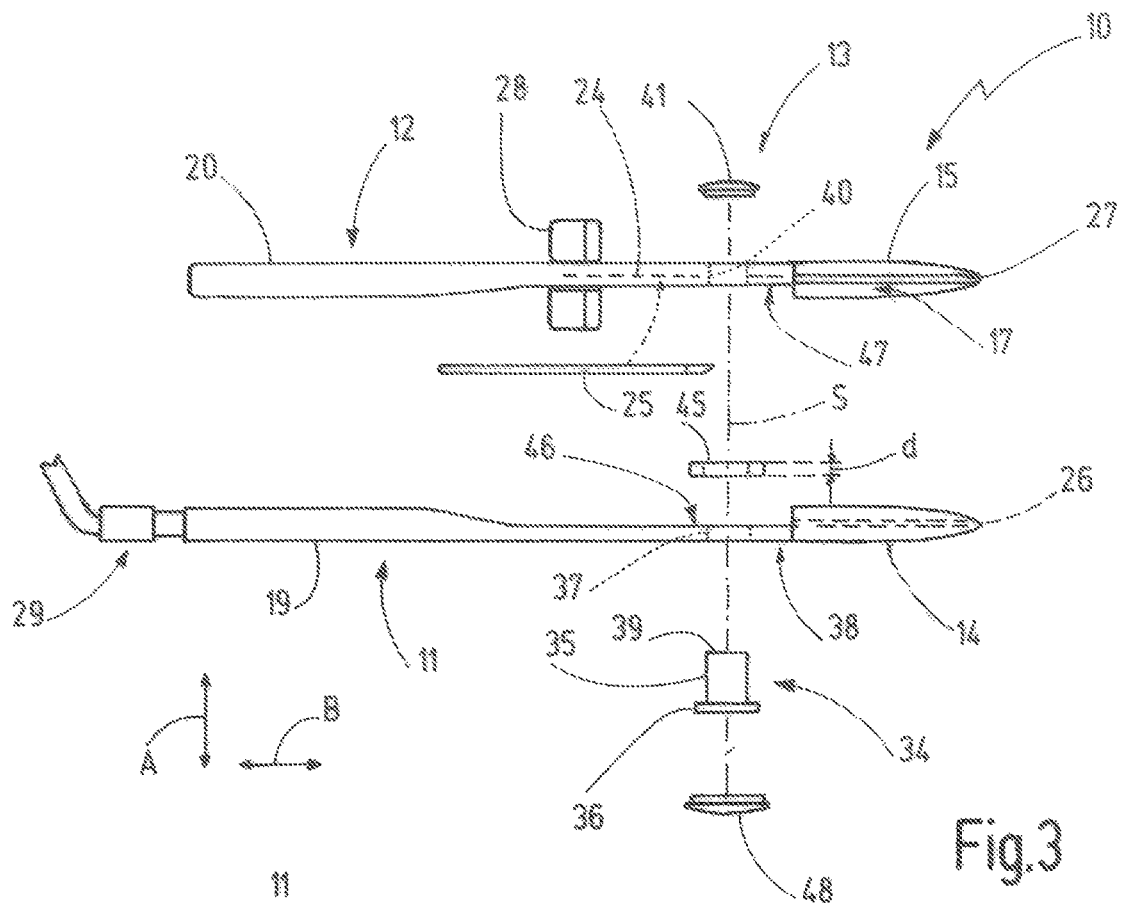

In FIG. 2 another embodiment of an electrosurgical instrument 10 is illustrated that is configured like scissors. FIG. 3 shows the embodiment of FIG. 2 in a schematic explosion diagram. In this embodiment the first branch 11 comprises the first jaw originating at the pivot axis S in direction toward the distal end and a first operation part 19 originating at the pivot axis S in direction toward the proximal end. Accordingly, the second branch 12 comprises the second jaw 15 originating from the pivot axis S in direction toward the distal end and a second operation path 20 originating at the pivot axis S in direction toward the proximal end.

In one of the branches and according to the example in the first branch 11, in addition a knife guide cavity 24 is provided that extends in the area of the pivot joint 13 and from the pivot joint 13 away in direction toward the proximal end of the first operation part 19. In the knife guide cavity 24 a knife 25 (FIG. 3) is movably supported in a guided manner in a movement direction B. The knife guide cavity 24 is continued in a first guide recess 26 in the first jaw 14 and in a second guide recess 27 in the second jaw 15. The knife 25 can be moved in movement direction B out of the knife guide cavity 24 along the guide recesses 26, 27 by means of a knife actuation device 28. Tissue held or clamped between the tissue contact surfaces 17, 18 can then be separated by the knife 25.

As apparent in FIG. 2, the pivot joint 13 or the pivot axis S is arranged offset from the knife guide cavity 24 transverse to the movement direction B. Thus, the knife guide cavity 24 extends past the pivot joint 13.

An electric connection device is illustrated in FIGS. 1 and 2 that is configured to be connected with an external plug or another suitable connection. The connection device 29 is preferably arranged at one of the branches in case of a scissors-like electrosurgical instrument and according to the example at the first branch 11 at the proximal end and thus at the first operation part 19. Via not disclosed conductors within the first branch 11 the two tissue contact surfaces 17, 18 are electrically connected with the electric connection device 29.

In an embodiment the electric circuit can be closed by means of an additional neutral electrode on the body of the patient (monopolar RF clamping instrument). In doing so, the two tissue contact surfaces 17, 18 have the same electric potential. It is not necessary to electrically isolate the area of the joint internally.

In an instrument 10 that is configured as bipolar instrument, the electric circuit between the two tissue contact surfaces 17, 18 is closed via the tissue in abutment therewith. Two conductors are guided to the joint via the connection device 29. The current transmission and/or voltage potential application to the tissue contact surface 18 of the second branch 12 is realized in the area of the joint. In doing so, preferably an electric insulation is provided in the area of the joint, particularly to guarantee the separation of the electric potential.

In the embodiment of FIG. 1 the electric connection device 29 is arranged at the operation unit 16 and the electric conductor extend originating from the operation unit 16 to the tissue contact surfaces 17, 18. The configuration of an embodiment of the pivot joint 13 is illustrated in the explosion diagram in FIG. 3 and in a perspective sectional view along the pivot axis S and orthogonal to the movement direction B in FIG. 4. In this embodiment the pivot joint 13 comprises a separate support pin 34. The support pin 34 has a circular cylindrical axle section 35 extending coaxially to the pivot axis S. At an axial end the support pin 34 has a head 36 having a larger dimension orthogonal to the pivot axis S as the axle section 35. For example, the head 36 can be formed by a disc-shaped and particularly circular ring-disc-shaped part of the support pin 34. The axle section 35 and the head 36 can be integrally formed or can be formed by separate components that are rigidly connected with each other.

The first branch 11 has a support cavity 37 through which the axle section 35 of the support pin 34 extends in a rotatably supported manner. The head 26 abuts at an outer surface 38 of the first branch 11 facing away from the second branch 12. The free end 39 of the support pin 34 opposite the head 36 extends in a through-hole 40 of the second branch 12 or passes through the through-hole 40. The free end 39 is connected with an end part 41 that comprises at least in sections a larger dimension than the through-hole 40 transverse to the pivot axis S. The end part 41 and/or the support pin 34 can be rigidly connected with the second branch 12, e.g. by means of welding and/or gluing and/or a press fit and/or another suitable connection. In doing so, the support pin 34 is secured against an undesired movement in axial direction A parallel to the pivot axis S. The end part 41 can be rigidly connected with the support pin 34, e.g. by welding and/or gluing and/or a press fit and/or another suitable connection. In the embodiment illustrated in FIGS. 3 and 4 the end part 41 has a disc-shaped or plate-shaped or cap-shaped form.

The second branch 12 and the support pin 34 have the same electric potential. According to the example, the end part 41 effects an electric insulation of the free end 39 of the support pin 34 to the outside and serves as touch guard. The electric insulation of the free end 39 of the support pin 34 can also be achieved by other means, e.g. by covering the free end 39 with insulation material, such as an adhesive. The adhesive can take a form that is identical or similar to the end part 41 after its curing, e.g. a cap-shaped form. In such an embodiment the end part 41 does not need to provide a securing effect of the support pin 34 against an undesired movement in axial direction A parallel to the pivot axis S. The axle section 35 of the support pin 34 can be directly fixed or secured at the through-hole 40 of the second branch 12.

The end part 41 is optional. It may also only have an exclusive electrically insulating effect. In this case, the joined axle is directly connected with the second branch 12, e.g. by welding. In this embodiment the end part 41 corresponds substantially to a cap. Alternatively or additionally, the end part 41 can also comply with the mechanical requirements as explained above and can retain the joint axially.

Figure 12:
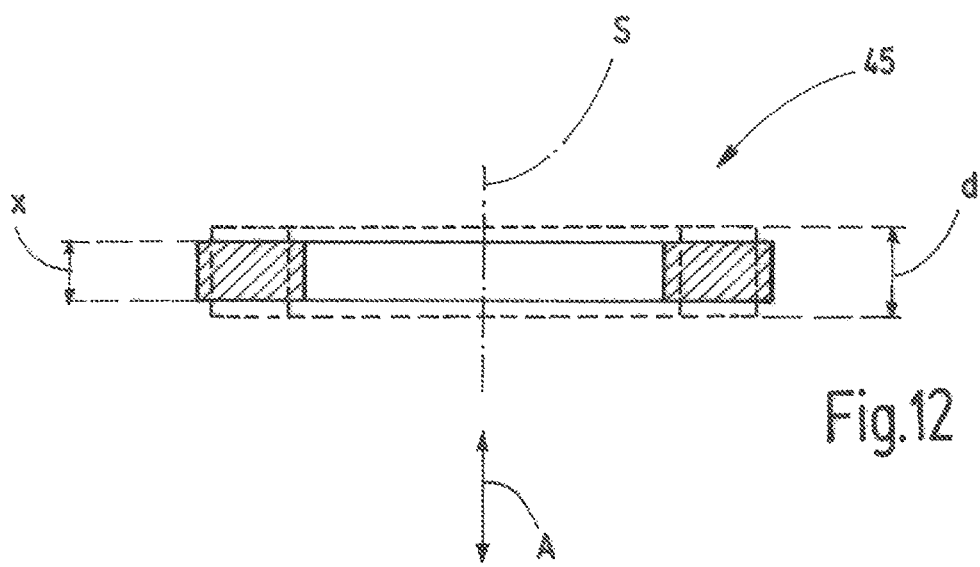

The electrosurgical instrument 10 also comprises a seal 45 that is closed in circumferential direction about the pivot axis S in a ring-shaped manner. The seal 45 can have a circular ring-shaped contour. In FIG. 12 the seal 45 is schematically illustrated in the cross-section. The shape of the seal 45 in an elastically non-deformed initial condition is illustrated in dashed lines. In axial direction A parallel to the pivot axis S the seal 45 has an axial thickness D. In the assembled condition between the two branches 11, 12 the seal 45 is compressed in axial direction A and its thickness is reduced. Due to this compression in axial direction A, the cross-sectional dimension of the seal 45 radial to the pivot axis S increases, as schematically illustrated in FIG. 12. The seal 45 shown in solid lines and hatched cross-sectional areas corresponds to the condition compressed in axial direction A.

The seal 45 abuts in axial direction A at a first abutment surface 46 at the first branch 11 and at the opposite side in axial direction A at a second abutment surface 47 of the second branch 12 in a sealing manner. The first abutment surface 46 surrounds the support cavity 37 in a ring-shaped manner. The second abutment surface 47 surrounds the through-hole 40 in a ring-shaped manner. The first abutment surface 46 and the second abutment surface 47 face each other and are arranged in axial direction A with an axial distance X between each other. Thus, the seal 45 has a thickness in axial direction A in the compressed condition that corresponds to the axial distance X between the first abutment surface 46 and the second abutment surface 47.

Preferably the axial distance X has a length of at least 0.1 mm and at most 0.4 mm. In the embodiment illustrated here the axial distance X is about 0.2 mm. In the non-deformed initial condition the seal 45 has an axial thickness D that is, e.g. 0.1 mm to 0.2 mm larger than the axial distance X (FIG. 12). Preferably the axial thickness D is in the non-deformed initial condition at least 25% larger or at least 50% larger or at least 100% larger than the axial distance X. It is further preferred, if the axial thickness D in the non-deformed initial condition is at most 200% larger than the axial distance X.

According to the example, the seal 45 has a rectangular cross-section and can thus be denoted also as seal disc. In one embodiment its hardness has an amount of 60 Shore. Preferably the seal 45 consists of a plastic material or a composite material or silicon. The seal 45 is permeable for steam and ethylene oxide (ETO). The material of the seal 45 is temperature resistant for temperatures in the range of 140° C. up to 250° C. or up to 300° C. or up to 400° C.

By means of the seal 45, the support area between the two branches is sealed. Contaminants cannot enter, or only in less amounts, the support gap between the support pin 34 and the support cavity 37 or the through-hole 40 between the two branches 11, 12.

In order to avoid the entering of contaminants also at the axial ends, i.e. the head 36 and the free end 39, in the embodiment the support pin 34 is sealed in the area of the axial end 39, e.g. by means of the cap-shaped end part 41 and/or an adhesive connection and/or a welding connection with the second branch 12. The end part 41 can abut sealingly tightly at the second branch 12 and is preferably sealingly connected with the second branch 12 by an adhesive connection, bond connection or welded connection. For example, an adhesive connection or welded connection can be present that extend all around in circumferential direction.

In order to seal the support pin 34 in the area of the head 36, a cap 48 is present in this embodiment that covers the head 36 and that sealingly abuts at the first branch 11 and according to the example at the outer surface 38 of the first branch 11. The cap 48 can be rigidly connected with the first branch 11, e.g. by a bond connection, an adhesive connection, a welded connection or the like, in order to avoid the entering of contaminants between the cap 48 and the first branch 11. For example, an adhesive connection or welded connection can be provided extending all around in circumferential direction. The support pin 34 can be rotatably arranged about the pivot axis S relative to the cap 48.

In the outer surface 38 a first cavity 49 can be introduced, in which a head 36 and a ring 50 surrounding the head 36 in circumferential direction about the pivot axis S can be at least partly accommodated. The cap 48 has a circumferential edge 51 that extends originating from the ring 50 radially outward away from the pivot axis S and abuts outside the first cavity 49 at the outer surface 38.

For the rotational support a bushing 52 can be provided between the axle section 35 and the first branch 11. This bushing 52 is, e.g. electrically insulated relative to the first branch 11. One of the electric conductors that originates from the connection device 29 is connected with the bushing 52. The bushing 52 forms a sliding contact for the support pin 34. Thus, an electric connection to the second branch 12 can be established via the support pin 34.

The end part 41 has a central section 53 that has according to the example a cylindrical shape and is accommodated in a second cavity 54 in an outer surface 55 of the second branch 12 facing away from the first branch 11. A circumferential edge 56 of the end part 41 surrounds the pivot axis S and extends originating from the central section 53 radially outward away from the pivot axis S. The circumferential edge 56 is arranged outside the second cavity 54 and abuts at the outer surface 55 of the second branch 12.

The branches 11 and 12 preferably comprise a metal core that provides a structural stiffness and can also be used as current conductor. The outer surfaces of branches 11 and 12, i.e. also the outer surfaces 38 and 55, are according to the example electrically non-conductive and are electrically insulated relative to the metal core. The metal core is, e.g. coated, overcasted or overmolded.

Thus, the pivot joint 13 is secured against the entering of contaminants in the area of the joint at the axial ends as well as between the branches 11, 12 by means of the seal 45. In doing so, the cleaning of such an electrosurgical instrument 10 is simplified.

In order to guarantee a defined axial distance X between the first abutment surface 46 and the second abutment surface 47, the first branch 11 and/or the second branch 12 comprise at least one distance element 60 that extends in axial direction A. In the embodiment illustrated in FIG. 4 one of the provided distance elements 60 is shown in the cross-sectional plane that is an integral part of the second branch 12 and extends away from the second branch 12 toward the first branch 11.

Each distance element 60 is rigidly connected with one of the two branches 11 or 12. In the embodiment illustrated here all of the distance elements 60 are rigidly connected with the second branch 12 and preferably integral part of the second branch 12, e.g. of a plastic body or plastic coating of the second branch 12. Each distance element 60 can also be part of a metal core of one of the branches 11, 12. The metal core is in this case coated, overcast or overmolded or electrically insulated toward the outside in any other manner, e.g. by means of a plastic body or plastic coating. Preferably multiple distance elements 60 are present. As it is apparent in FIG. 6, according to the example, three distance elements 60 are provided at the second branch 12 that are arranged with distance to each other in circumferential direction about the pivot axis S. The radial distance between the pivot axis S and the distance elements 60 can be equal or can have different lengths. Preferably the distance elements 60 are arranged along a common circumcircle line in circumferential direction about the pivot axis S and are distributed regularly about the pivot axis S. In this manner the branches 11, 12 or the jaws 14, 15 of the two branches 11, 12 are secured against an unintended tilting relative to each other. Due to the distances in circumferential direction between the distance elements 60 and due to a preferably provided radial distance to the seal 45, sufficient space is provided for purging with a purge liquid by means of which the cleaning is improved.

In an embodiment at least some of the distance elements 60 can have a cylindrical contour.

Each distance element 60 has an end surface 61 that faces the first branch 11 and slidingly abuts at the first branch 11 in the embodiment. The end surface 61 extends, according to the example, in a plane orthogonal to the pivot axis S. The end surface can alternatively to this also be convexly curved.

The end surface 61 of each distance element 60 forms a friction bearing surface 62 for the first branch 11. During pivoting of the two branches 11, 12 about the pivot axis S relative to each other the first branch 11 slides at the friction bearing surfaces 62 of the distance elements 60 on a circular arc-shaped path about the pivot axis S respectively.

Figure 6:
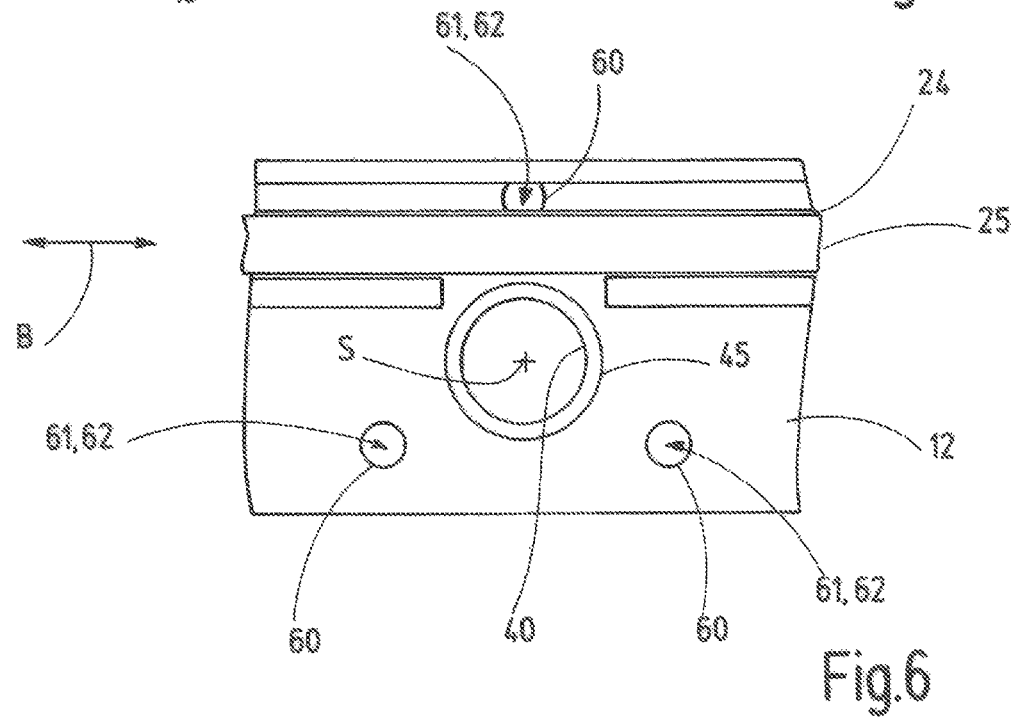
Figure 11:
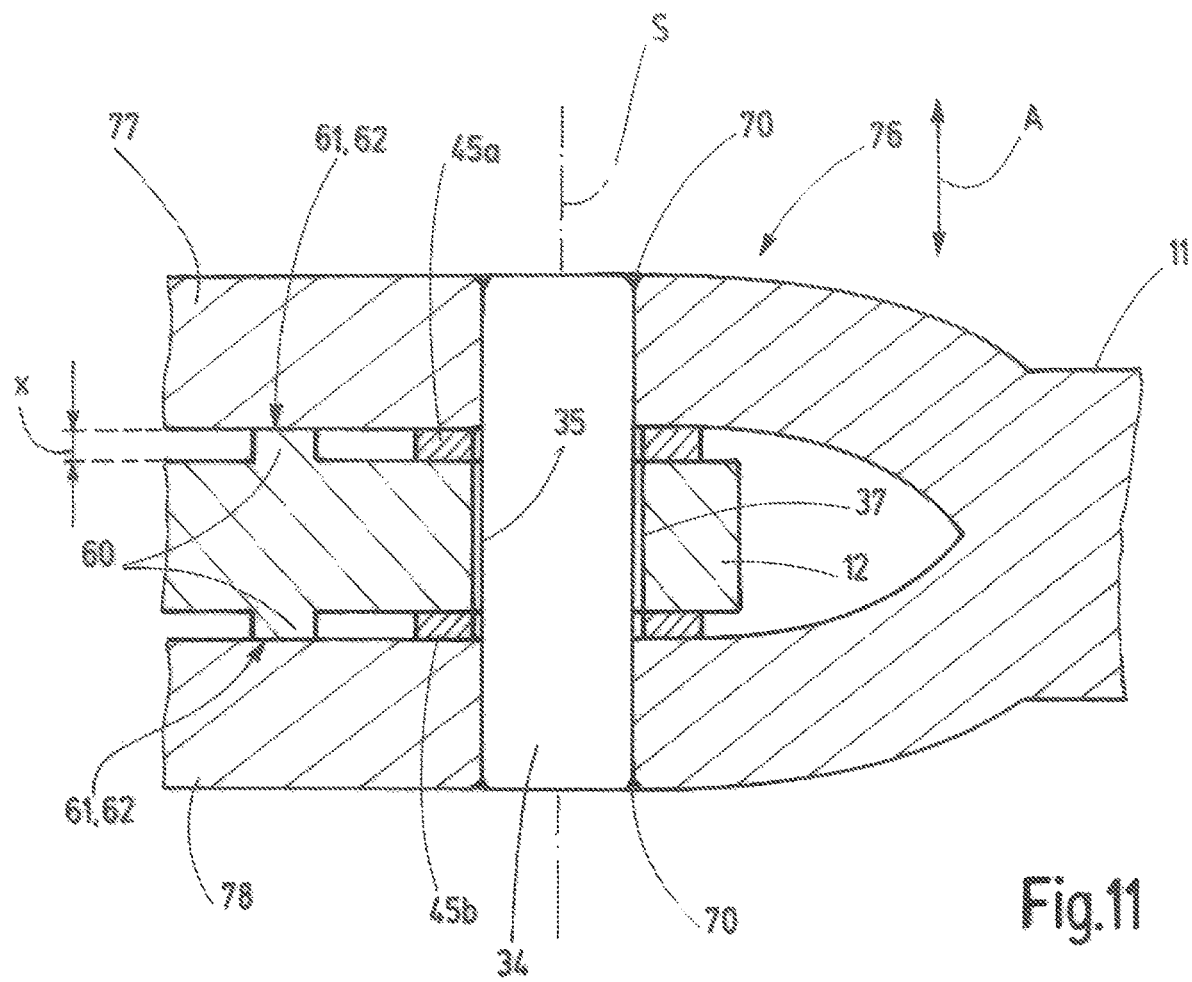

It has to be noted that the contour, the number and the arrangement of the distance element 60 can also be different from the illustration in FIG. 6 in other embodiments.

In FIG. 6 it is also apparent that the knife guide cavity 24 extends between one of the distance elements 60 and the pivot axis S in movement direction B. This arrangement is advantageous, because the distance of the knife guide cavity 24 from the pivot axis S shall be selected as small as possible. The available space between the outer circumference of the seal 45 and the knife guide cavity 24 or the knife 25 may thus not be sufficient for arranging of a distance element 60 that is, according to the example, therefore provided at the other side of the knife guide cavity 24.

Figure 4:
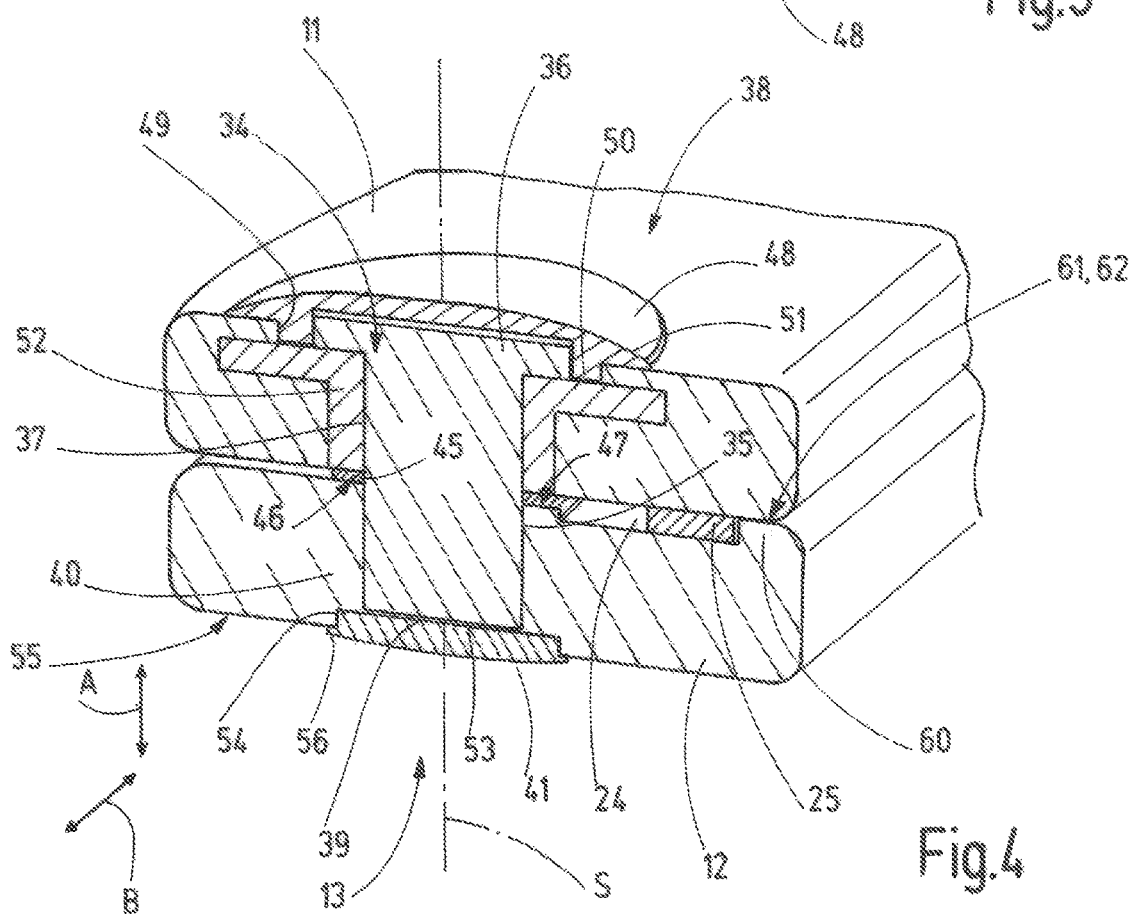
Figure 5:
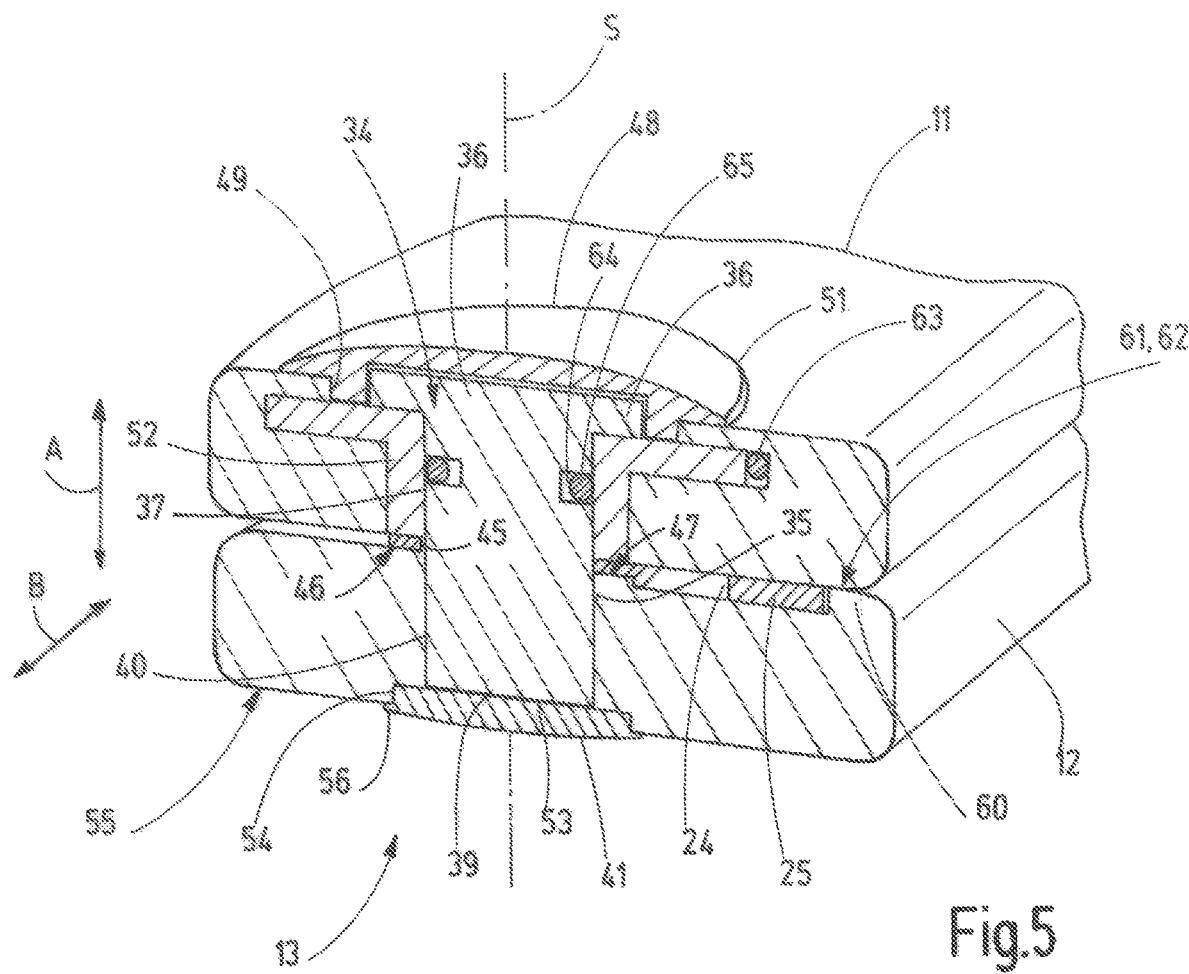

In FIG. 5 an embodiment is illustrated that is modified compared with the example of FIG. 4. As far as the embodiments coincide, reference is made to the description above. In addition to the embodiment shown in FIG. 4 and illustrated so far, a possibility of the electric contacting of a conductor 63 with the support pin 34 is illustrated. The conductor 63 extends, according to the example, along the first branch 11 as far as the bushing 52 and is electrically conductively connected with the bushing 52. The bushing 52 is electrically conductive. Because of the pivot joint play between the bushing 52 and the support pin 34, preferably a spring contact 65 can be arranged in a ring cavity 64 that is on one hand electrically conductively connected with the support pin 34 and on the other hand biased radially outward away from the pivot axis S against an inner surface 52.

In FIGS. 7 to 11 additional embodiments for realizing of the pivot joint 13 are highly schematically illustrated in a cross-section along the pivot axis S orthogonal to the movement direction B.

In the embodiment shown in FIG. 7 the free end 39 of the support pin 34 is connected with the second branch 12 by joint 70 that extends all around, e.g. a welded joint or adhesive joint such that the entering of contaminants in the gap between the support pin 34 and the through-hole 40 is avoided. Another joint 70 extending all around is provided between the first branch 11 and the cap 48 that can also be realized as welded joint or adhesive joint.

In this embodiment the distance elements 60 are provided at the first branch 11 or are integral part thereof different to the embodiments described so far.

The embodiment that is schematically illustrated in FIG. 8 provides the at least one distance element 60 is arranged at the second branch 12 or is integral part thereof. In this embodiment the support pin 34 is also integral part of one of the branches 11, 12 and according to the example of the second branch 12. The through-hole 40 and the head 36 are omitted. According to the example, the axle section 35 extends away from the second abutment surface 47 through the support cavity 37 to the free end 39. In this embodiment the free end 39 extends out of the support cavity 37 and is secured by means of the end part 41 that can be disc-shaped according to the example, and/or the axle section 35. The disc-shaped end part 41 is sealingly and rigidly connected via a joint 70 extending all around with the free end 39 or the axle section 35 of the support pin 34. The end part 41 abuts over a ring area with a sufficient radial dimension at the outer surface 38 of the first branch 11 by formation of a friction connection in a sealing manner. In doing so, the entering of contaminants in the support gap between the axle section 35 and the support cavity 37 is at least hindered or avoided.

The embodiment of the pivot joint 13 schematically illustrated in FIG. 9 comprises a support pin 34, at which the at least one distance element 60 is formed by at least one radial projection 71 that protrudes relative to the axle section 35 radially outward from the pivot axis S. In the embodiment illustrated in FIG. 9 one single radial projection 71 is provided that extends all around such that it therefore forms a ring collar. Also multiple radial projections 71 could be provided arranged with distance to each other in circumferential direction about the pivot axis S, particularly at least three such radial projections 71.

In another embodiment the at least one distance element 60 is arranged with view radial to the pivot axis S between the seal 45 and the pivot axis S. The at least one distance element 60 can be surrounded by the seal 45 and can be arranged so-to-speak in the sealed area of the pivot joint 13. This configuration is also possible by modification of one of the embodiments of FIGS. 7, 8 and 10 by arranging the at least one distance element 60 radially further inward than the seal 45 or by arranging the at least one distance element 60 centrally.

At the at least one radial projection 71 the friction bearing surface 62 is provided that serves for sliding abutment with one of the branches, according to the example with the first branch 11. Different to the embodiments described so far, therefore, the at least one distance element 60 is not provided at one of the branches, but at the support pin 34. The distance element 60 is located in the area sealed by the seal 45. With view radially to the pivot axis S, the seal 45 is further away from the pivot axis S as the radial projection 71.

In the area of the free end 39 the axle section 35 of the support pin 34 extends out of the support cavity 37 and is there sealingly connected with an end part 41 by a joint 70 extending all around similar to the embodiment of FIG. 8. Different to the embodiment of FIG. 8, the end part 41 is in this embodiment configured as biasing element 72 that creates a biasing force between the two branches 11, 12. The biasing element 72 creates a biasing force in axial direction A on the support pin 34 and thus urges the friction bearing surface 62 against the first branch 11. At the end opposite the free end 39, the support pin 34 is rigidly connected with the second branch 12 by means of a joint 70 extending all around, particularly in the area of the outer surface 55 of the second branch 12. Thus, it can be guaranteed by means of the biasing element 72 that also in spite of manufacturing tolerances and/or wear and/or shrinking processes, the axial distance X is either maintained or intentionally decreased in order to ensure the sealing effect of the seal 45 furthermore.

It is also apparent in FIG. 9 that the seal 45 can be arranged in a depression 73. In the embodiment the depression 73 can be provided in the first branch 11. The depression 73 is open toward the second abutment surface 47 of the second branch 12. The bottom of the depression 73 forms at least a section of the first abutment surface 46. Additionally or alternatively, a depression 73 could also be provided in the second branch 12. The at least one depression 73 has the advantage that the axial thickness D of the seal 45 in the non-deformed initial condition can be selected larger and thus a longer compression path or compression stroke is available without the need to increase the axial dimensions of the electrosurgical instrument in axial direction A. In addition, the position of the seal 45 orthogonal to the pivot axis S or the support pin 34 can be defined and maintained by the at least one depression 73.

In the embodiment of FIG. 9, in addition to the distance element 60 formed at the support pin 34, additional measures can be provided for sterilizing the pivot joint 13, e.g. against undesired tilting. For example, additional distance elements 60 can be provided such as illustrated in FIGS. 4 to 8. Such additional distance elements 60 would have, e.g. only the task to stabilize, but not to limit or to adjust the axial compression of the seal 45.

The embodiment of the pivot joint 13 illustrated in FIG. 10 corresponds substantially to the embodiment according to FIG. 8. Different to the embodiment of FIG. 8, the embodiment illustrated in FIG. 10 is provided with an additional seal element 74. The additional seal element 74 is, according to the example, arranged between the end part 41 and the first branch 11 or the outer surface 38 of the first branch 11. The additional seal element 74 can be configured corresponding to the seal 45. The additional seal element 74 surrounds the free end 39 extending out of the support cavity 37 or the axle section 35 of the support pin 34 completely and seals the gap between the end part 41 and the first branch 11. Apart therefrom reference can be made to the description of FIG. 8. The additional seal element 74 can also be used as another modified embodiment of the embodiment shown in FIG. 9.

The embodiments of the pivot joint 13 described so far refer to a single side support. The first branch 11 and the second branch 12 are thereby arranged next to each other along the pivot axis S without meshing with each other. In the embodiment illustrated in FIG. 11 one of the branches and, e.g. the first branch 11 has in the region of the pivot joint 13 a fork part 76 with a first arm 77 and a second arm 78 that are arranged with distance to each other in axial direction A. The support pin 34 passes through the two arms 77, 78 and is at the respective axial end rigidly and sealingly connected with the arms 77 or 78 by a joint 70 extending all around, particularly a welded joint or an adhesive joint. The second branch 12 with the support cavity 37 extends in the free space between the arms 77, 78, wherein the axle section 35 of the support pin 34 passes through the support cavity 37. A first seal 45a is arranged between the second branch 12 and the first arm 77 and a second seal 45b is arranged between the second branch 12 and the second arm 78 and respectively abut sealingly between the respective arm 77 or 78 on one side and the second branch 12 on the other side. At least between one of the two arms 77, 78 and according to the example between both arms 77, 78 and the second branch 12, as an option at least one distance element 60 can be arranged in order to define the axial distance X analog to the embodiments described so far and to define the axial compression of the seals 45a, 45b.

It has to be noted that embodiments of the pivot joint 13 illustrated in the drawings can also be combined with each other. For example, in each embodiment at least one depression 73 for reception of a seal 45 can be provided.

In each embodiment of the pivot joint 13 a biasing element 72 can be provided in order to bias or urge the two branches 11, 12 in axial direction A toward each other with a biasing force. In addition in each embodiment an additional seal element 74 can also be provided in order to seal the area of the axial end and particularly the free end 39 of the support pin 34 relative to the support gap between the axle section 35 and the support cavity 37.

The invention refers to an electrosurgical instrument 10 with two branches 11, 12 that are pivotably supported at each other by means of a pivot joint 13. The pivot joint 13 has a support pin 34 and a support cavity 37. The support pin 34 is particularly torque-proof connected with one of the branches 11 or 12 and rotatably supported in the support cavity 37 of the respective other branch 12 or 11. Between the branches 11, 12 a seal 45 is provided that sealingly abuts at the two branches 11, 12 and that surrounds the support pin 34 completely in circumferential direction. Preferably the support pin 34 is sealingly connected with the respective branch 11, 12 at its axial ends. In doing so, entering of contaminants in the area between the support pin 34 and the support cavity 37 from all sides or access possibilities is avoided or at least reduced.

List Of Reference Signs 10 electrosurgical Instrument
11 first branch
12 second branch
13 pivot joint
14 first jaw
15 second jaw
16 operation unit
17 first tissue contact surface
18 second tissue contact surface
19 first operation part
20 second operation part
24 knife guide cavity
25 knife
26 first guide recess
27 second guide recess
28 knife actuation device
29 electric connection device
34 support pin
35 axle section of support pin
36 head of support pin
37 support cavity
38 outer surface of first branch
39 free end of support pin
40 through-hole
41 end part
45 seal
45a first seal
45b second seal
46 first abutment surface
47 second abutment surface
48 cap
49 first cavity
50 ring of cap
51 circumferential edge
52 bushing
53 central section
54 second cavity
55 outer surface of second branch
56 circumferential edge
60 distance element
61 end surface
62 friction bearing surface
63 conductor
64 ring cavity
65 spring contact
70 joint
71 radial projection
72 biasing element
73 depression
74 additional seal element
76 fork part
77 first arm 78 second arm
A axial direction
d axial thickness
S pivot axis
x axial distance

The invention claimed is:

1. An electrosurgical instrument (10), comprising:
a first branch (11) and a second branch (12) that are pivotably arranged about a pivot axis (S) at a pivot joint (13), wherein the pivot joint (13) comprises a support pin (34) and a support cavity (37) formed in at least one of the first and second branches in which the support pin is received, and
An elastically deformable seal (45) that completely surrounds the support pin (34) in a circumferential direction about the pivot axis (S) and sealingly abuts against a first abutment surface (46) of the first branch (11) and an opposing second abutment surface (47) of the second branch (12) so as to inhibit entry of contaminants into a space between the support pin (34) and the support cavity (37),
wherein the elastically deformable seal (45) is compressed between the first abutment surface and the opposing second abutment surface (46, 47) of the first and second branches (11, 12) such that the elastically deformable seal (45) is elastically deformed therebetween in an axial direction (A) parallel to the pivot axis (S).

2. The electrosurgical instrument according to claim 1, further comprising at least one distance element (60) that extends in an axial direction (A) parallel to the pivot axis (S) and defines an axial distance (X) between the first abutment surface (46) and the second abutment surface (47).

3. The electrosurgical instrument according to claim 2, wherein the at least one distance element (60) is rigidly connected with one of the branches (11, 12).

4. The electrosurgical instrument according to claim 2, wherein the at least one distance element comprises an end surface (61) at a free end that forms a friction bearing surface (62) and abuts the first branch (11) or the second branch (12).

5. The electrosurgical instrument according to claim 2, wherein the at least one distance element comprises at least three distance elements (60) that are arranged at a distance with respect to each other in the circumferential direction about the pivot axis (S).

6. The electrosurgical instrument according to claim 2, wherein the elastically deformable seal (45) comprises an axial thickness (D) in an undeformed initial condition that is larger than the axial distance (X).

7. The electrosurgical instrument according to claim 1, further comprising a depression (73) in the first branch (11) and/or the second branch (12) for reception of the elastically deformable seal (45).

8. The electrosurgical instrument according to claim 1, wherein the elastically deformable seal (45) has a rectangular cross-section.

9. The electrosurgical instrument according to claim 1, further comprising a knife guide cavity (24) in the first branch (11) and/or the second branch (12), in which a knife (25) is movably supported in a movement direction (B) in a guided manner.

10. The electrosurgical instrument according to claim 9, wherein the support pin (34) is arranged offset to the knife guide cavity (24).

11. The electrosurgical instrument according to claim 1, further comprising a biasing element (72) that urges the first branch (11) and the second branch (12) toward each other in an axial direction (A) parallel to the pivot axis (S).

12. The electrosurgical instrument according to claim 1, wherein the support pin (34) is connected in a torque-proof manner with the first branch (11) or the second branch (12) and is rotatably supported in a support cavity (37) of the respective other of the second branch (12) or the first branch (11).

13. The electrosurgical instrument according to claim 12, further comprising an area between the support cavity (37) and the support pin (34) that is sealed by an additional seal element (74).

* * * * *